United States Patent [19]

Gould

[11] Patent Number: 4,806,475

[45] Date of Patent: * Feb. 21, 1989

[54] ALKALINE PEROXIDE TREATMENT OF AGRICULTURAL BYPRODUCTS

[75] Inventor: John M. Gould, Brimfield, Ill.

[73] Assignee: The United States of America as represented by the Secretary of Agriculture, Washington, D.C.

[*] Notice: The portion of the term of this patent subsequent to Mar. 10, 2004 has been disclaimed.

[21] Appl. No.: 912,296

[22] Filed: Sep. 29, 1986

Related U.S. Application Data

[63] Continuation-in-part of Ser. No. 566,380, Dec. 28, 1983, Pat. No. 4,649,113.

[51] Int. Cl.$^4$ .......................... C12P 7/10; C13K 1/02; D21C 3/00; D01C 1/00
[52] U.S. Cl. ..................................... 435/165; 127/37; 162/78; 162/99
[58] Field of Search ...................... 435/165; 127/37; 530/500; 162/78, 99

[56] References Cited

U.S. PATENT DOCUMENTS

| | | | |
|---|---|---|---|
| 2,487,114 | 11/1949 | Dreyfus | 162/25 |
| 4,314,854 | 2/1982 | Takagi | 127/37 |
| 4,462,864 | 7/1984 | Carles et al. | 162/56 |
| 4,649,113 | 3/1987 | Gould | 435/165 |

FOREIGN PATENT DOCUMENTS 1169794 6/1984 Canada .

OTHER PUBLICATIONS

D. Lachenal et al., "Hydrogen Peroxide as a Delignifying Agent," Tappi 63(4): 119–122 (Apr. 1980).
"Peroxide Treatment of Lignocellulose," Northern Regional Research Center Notes from the Director, Issue 1533, pp. 1–2 (Jan. 28, 1983).
"Mix Straw with Hydrogen Peroxide, Soak Well and Serve-to Farm Animals?" Des Moines Sunday Register (Nov. 24, 1985).
"Can This Cellulose Mash Change Corn Grain's Role in Fattening Rations?" Beef (Mar. 1986).
"New Process Spins Crop Residue Into 'Golden' Products," Farm Industry News, pp. 12–13 (Apr. 1986).
J. M. Gould, "Alkaline Peroxide Delignification of Agricultural Residues to Enhance Enzymatic Saccharification," Biotech. Bioeng. XXVI: 46–52 (1984); #5350.
J. M. Gould et al., "High–Efficiency Production from Lignocellulosic Residues Pretreated with Alkaline $H_2O_2$," Biotech. Biotech. Bioeng. XXVI: 628–631 (1984); #5387.
J. M. Gould, "Studies on the Mechanism of Alkaline Peroxide Delignification of Agricultural Residues," Biotech. Bioeng. XXVII: 225–231 (1985); #5530.
J. M. Gould, "Enhanced Polysaccharide Recovery from Agricultural Residues and Perennial Grasses Treated with Alkaline Hydrogen Peroxide," Biotech. Bioeng. XXVII: 893–896 (1985); #5560.
M. S. Kerley et al., "Alkaline Hydrogen Peroxide Treatment Unlocks Energy in Agricultural By-Products," Science 230: 820–822 (Nov. 15, 1985); #5605.
"'Peoria Diet' Starts with Corn Stalks," Peoria Journal Star, pp. A14 and A2 (Jun. 7, 1986).

*Primary Examiner*—Esther M. Kepplinger
*Assistant Examiner*—Janelle Graeter
*Attorney, Agent, or Firm*—M. Howard Silverstein; David G. McConnell; Curtis P. Ribando

[57] ABSTRACT

Nonwoody lignocellulosic portions of plant fruits, roots, and tubers, such as sugar beet pulp, citrus pulp, seed hulls, and cereal bran are treated with hydrogen peroxide under alkaline conditions thereby delignifying the materials and rendering the cellulose and hemicellulose highly available for subsequent use. The products are characterized by enhanced water-binding capacity of the cellulose as indicated by high water swellability. The products are also nontoxic and thereby useful as carbohydrate sources in ruminant feeds, as microbial feedstocks, and as sources of dietary fiber for humans and other monogastrics.

18 Claims, No Drawings

ALKALINE PEROXIDE TREATMENT OF AGRICULTURAL BYPRODUCTS

CROSS-REFERENCE TO RELATED APPLICATION

This application is a continuation-in-part of Ser. No. 06/566,380, filed Dec. 28, 1983, now U.S. Pat. No. 4,649,113.

BACKGROUND OF THE INVENTION

1. Field of the Invention

Agricultural byproducts such as sugar beet pulp, citrus fruit pulp, seed hulls, and cereal bran exiting as waste streams from commercial crop processing plants have little inherent value and have traditionally constituted a disposal problem. These materials represent an abundant, inexpensive, and readily available source of renewable lignocellulosic biomass. However, their utilization as a carbohydrate source for glucose and ethanol production, and as a metabolic energy source in ruminant feeds, has been severely hampered by the low efficiency with which organisms and enzymes are able to convert the polysaccharide portion of the residue into monomeric sugars. The low conversion efficiency for lignocellulosic materials is the result of two principal factors: (1) unavailability of the cellulose and hemicellulose resulting from the close physical and chemical association between lignin and these polysaccharides in the plant cell wall, and (2) the degree of crystallinity within the cellulose polymer itself.

Lignin is thought to prevent the degradation of cellulose mainly by acting as a physical barrier between the cellulolytic enzyme and its substrate. Consequently, the rate and extent of enzymatic cellulose degradation in lignocellulosic materials is inversely related to the lignin content, with maximum degradation occurring only after 50% or more of the lignin has been removed. Even when lignin levels are low, however, the hydrolysis of cellulose can be limited by the physical properties of the polysaccharide itself. Amorphous regions of cellulose are hydrolyzed at much higher rates than are microcrystalline regions, for example.

This invention relates to a pretreatment process for rendering the polysaccharide components of nonwoody lignocellulosic residues available for use in biological systems as sources of carbohydrate.

2. Description of the Prior Art

Numerous pretreatments have been developed in an effort to increase the efficiency of enzymatic saccharification. These processes utilize physical, chemical, and/or biological methods to remove lignin and decrease cellulose crystallinity. Although most of these pretreatments do result in increased cellulose hydrolysis, the yields of glucose obtained are usually still well below theoretical levels. Moreover, processes such as autohydrolysis, alkaline cooking, and steam explosion require substantial energy input in the form of heat and tend to generate toxic side products. A few pretreatments have been developed that allow essentially quantitative conversion of cellulose into glucose, but these processes involve the use of expensive, highly toxic reagents such as cadoxen, ethylenediamine, or peracetic acid. Toxic constituents in the digest, of course, interfere with subsequent biological saccharification and fermentation steps, and also prohibit use of the digest as an animal feed. Other drawbacks typical of conventional pretreatments include loss of the hemicellulose with the solubilized fraction and also reversion of the cellulose crystallinity upon drying.

In nature, lignin is degraded by various organisms, primarily to increase the amount of cellulose available for enzymatic digestion. Although the mechanism of natural lignin degradation is largely unknown, it is thought that oxidants such as $H_2O_2$ may play an important role [Tien et al., Science 221: 661–662 Aug. 12, 1983)]. Hydrogen peroxide is known to react with lignin under certain conditions and has been widely used for many years to bleach high-lignin wood pulps. More recently, Lachenal et al. [Tappi 63(4): 119–122 (April 1980)] have found that at 80°–120° C. under alkaline conditions, $H_2O_2$ will delignify kraft pulps with partial degradation of the cellulose. However, failure to preserve the hemicellulose fraction and the requisite for high energy and reagent inputs diminish the appeal of applying the Lachenal et al. process to agricultural residues. Takagi (U.S. Pat. No. 4,314,854) observed that when cellulosic materials were treated with a combination of $H_2O_2$ and manganese salts, cellulosic materials were somewhat more susceptible to hydrolysis by cellulolytic enzymes but with no apparent advantage derived from the hemicellulose.

Dreyfus (U.S. Pat. No. 2,487,114) obtains a product high in alpha-cellulose content and low in hemicellulose by treating straw with hydrogen peroxide in highly alkaline aqueous solution. In the parent application referred to above, and incorporated herein by reference, a process is disclosed for efficiently converting leaves and stalks of nonwoody plants to useful carbohydrate sources for ruminants and microbes by treatment with alkaline peroxide. The treatment is under conditions of controlled pH which are designed to conserve the hemicellulose in the recovered carbohydrate fraction. Illustrative substrates useful in the process include agricultural residues and noncultivated grasses such as wheat straw, corn stalks, corn cobs, and prairie grass.

SUMMARY OF THE INVENTION

I have now discovered that certain nonwoody lignocellulosic portions of fruits, roots, and tubers can be converted with alkaline peroxide to useful carbohydrate sources for ruminants and microbes and to a dietary fiber source for humans and other monogastric animals. These byproducts can be categorized as nonwoody components of either woody or nonwoody plants. By virtue of the treatment, the substrate is not only delignified to the extent that virtually all of the polysaccharide is made available, but the crystallinity of the cellulose is permanently disrupted so as to render the product highly water swellable.

In accordance with this discovery, it is an object of the invention to provide a facile, delignification process which permits the efficient utilization of waste stream crop materials resulting from commercial separation processes.

Another object of the invention is to provide a nontoxic nutritional food source for ruminant animals.

A further object of the invention is to provide a microbial feedstock useful in the production of alcohol and other beneficial products.

It is also an object of the invention to provide a novel source of natural, dietary fiber for incorporation into ingestible formulations for nonruminants.

Other objects and advantages of this invention will become readily apparent from the ensuing description.

DETAILED DESCRIPTION OF THE INVENTION

The term "available" and its derivatives as used herein in reference to the terms "cellulose," "hemicellulose," and "polysaccharides" are defined as meaning "free" in the sense that these components of the substrate are accessible for enzymatic hydrolysis to monosaccharides under normal conditions and/or readily digestible by ruminant animals without prior modification. The term "woody" is used herein both in the botanical sense to mean "comprising wood;" that is, composed of extensive xylem tissue as found in trees and shrubs, and also in the sense of "being woodlike."

The terms "fruits," "roots," and "tubers" are used herein in the botanical sense. Thus, "fruit" is defined as the ripened plant ovary (or group of ovaries) containing the seeds, together with any adjacent parts that may be fused with it at maturity. It is intended that the term "fruit" include simple dry fruits (follicles, legumes, capsules, achenes, grains, samaras, and nuts), simple fleshy fruits (berries, drupes, false berries, and pomes), aggregate fruits, and multiple fruits, as botanically defined. For the purposes herein, the term "fruits" is also intended to include any residual or modified leaf and flower parts which may contain or be attached to the true fruit, such as a bract. Encompassed within this definition of "fruit" are cereal grains and other seeds. Components of these materials contemplated for use herein include bran and certain seed hulls. "Bran" is a component of cereals and is defined as a fraction obtained during the processing of cereal grain seeds and consisting of the lignocellulosic seedcoat separated from the flour or meal. Examples of nonwoody seed hulls are the bracts of oats and rice. "Root" is defined as the usually underground portion of a plant body that functions as an organ of absorption, aeration, and food storage or as a means of anchorage and support, and differs from the stem especially in lacking nodes, buds, and leaves. "Tuber" is defined as a much enlarged portion of a subterranian stem (stolon) provided with buds on the sides and tips.

The lignocellulosic substrates of principal interest are waste stream components from commercial processing of crop materials such as sugar beet pulp, citrus fruit pulp, nonwoody seed hulls, and cereal bran. Unless otherwise specified, the terms "citrus pulp" or "citrus fruit pulp" will be used herein in the generic sense to define the waste product of the citrus juice industry. This product typically includes both the rind of the fruit and also the fleshy juice sacs. The fleshy material is oftentimes also referred to as "pulp," and it alone is a suitable substrate within the ambit of the invention.

The substrate may be treated directly as recovered from the mill or processing plant or may optionally be subjected to one or more preparatory steps such as chopping or grinding to facilitate handling. In some cases, it may be necessary to clean the substrate by screening, washing, or the like in order to remove dirt, debris, and other undesirable matter.

The reaction is conducted in an aqueous medium in sufficient quantity to effect uniform wetting of the substrate. Typically, the substrate is suspended in the medium at concentrations ranging from about 20–300 g./l., with delignification being favored at the lower concentrations, particularly in the range of 20–100 g./l.

For optimum yield of available carbohydrate, it is critical that the pH of the resultant slurry be controlled within the range of about 11.2 to about 11.8, and preferably as close to 11.5 as possible. Below pH 11.2, the delignification efficiency declines significantly. Above pH 11.8 delignification may be slightly improved, but the saccharification efficiency is adversely affected. Also, at higher pH's (greater than 11.8), the hemicellulose begins to solubilize substantially, reducing the amount recovered with the cellulose in the insoluble fraction. Initial adjustment of the slurry pH to within the aforementioned range is readily accomplished by addition of sodium hydroxide or other strong alkali. Throughout the course of the reaction, the pH may tend to drift if not adjusted periodically. Allowing the pH to drift beyond the upper limit of the operable range is not detrimental to the results provided that it occurs only in the final stages of the reaction.

The degree or efficiency of delignification attainable by the process for a given substrate is limited to an intrinsic maximum, and at least in part is a function of the concentration of $H_2O_2$ in the reaction medium. Generally, the peroxide should be present in a ratio of peroxide to substrate of at least about 0.01 (w/w). The minimum amount of peroxide needed to achieve the maximum delignification can be readily determined by the skilled artisan.

The reaction of the alkaline peroxide with the lignocellulosic substrate proceeds at a relatively rapid rate at room temperature (25° C.), minimizing the requirement for energy input. Other temperatures within the range of 5° C. to at least 60° C. are also operable, with of course some variance in the rate of delignification. At optimum peroxide levels, pH 11.5, and 25° C., the delignification reaction is complete in less than 12 hr. Physical disintegration of the substrate is facilitated by application of mechanical shear such as that provided by a conventional stirring apparatus.

Upon completion of the reaction, the partially delignified insoluble fraction is recovered by filtration or centrifugation, and may be optionally washed with water and/or dried. The filtrate containing the solubilized lignin degradation products is suitable for recycle upon addition of makeup $H_2O_2$ and readjusting the pH as necessary. Typically about 40–60% of the original lignin content of the substrate is removed from the insoluble fraction and enters into the supernatant. The buildup of soluble lignin in continuously recycled medium has a negligible effect on the reagents' efficacy toward delignification. Characterization of the lignin degradation products reveals a high proportion of low molecular weight carboxylic acids. These acids have potential as chemical feedstocks, and reclamation thereof is considered an ancillary asset to the inventive process.

As compared to the original substrate, the recovered residue exhibits a significant increase in water absorbency, suggesting a corresponding decrease in the proportion of total cellulose contained in highly crystalline structures. It was surprising to find that, contrary to other treatments reducing cellulose crystallinity, the increase in cellulose water absorbency by the alkaline peroxide treatment is irreversible, such that the enhanced water absorbency persists even after drying. The increase in water absorbency is accompanied by a corresponding increase in swollen volume of the treated material. While not desiring to be bound to any particular theory of operation, the observed changes in the properties of the cellulose are thought to be the result of a modification of a small portion (<5%) of the glucose units such as to disrupt the hydrogen bonding pattern between chains, and thereby maintain a highly open structure. The freed hydroxyl groups become available for binding molecules of water, thereby enhancing what is referred to herein as the water-binding capacity of the cellulose.

By virtue of controlling the pH within the aforementioned range, the preponderance of the hemicellulose fraction remains insolubilized with the cellulose. The yield of these two components in the insoluble fraction approaches the theoretical amount. Their availability as indicated by nearly quantitative cellulose-to-glucose enzymatic conversion efficiencies approaches 100%.

The alkaline peroxide-treated product of this invention is useful as a microbial feedstock without the need for detoxification or any other type of purification. The glucosidic saccharification product is likewise free of inhibitory side products which would tend to interfere with microbial growth, and is efficiently fermented to ethanol or the like by conventional methods in the art. In combined saccharification/fermentation experiments using *Trichoderma reesei* cellulase and *Saccharomyces cerevisiae,* ethanol yields exceeding 90% of theoretical (based upon original cellulose content) have been obtained. The available polysaccharide also has potential in other microbial processes such as the production of single-cell protein.

In like manner, the delignified byproducts of the instant process are remarkably adapted for use as carbohydrate sources in ruminant feeds without purification or further treatment. Up to 100% of the potentially digestible matter is in fact digestible by the ruminant animal. The product is suitably blended with other feed components needed for a balanced diet.

The highly amorphous, water-absorbent product also lends itself to use as a noncaloric fiber source in the diets of humans and other monogastric animals. As such, it can be incorporated into foods in accordance with the procedures and advantages outlined in commonly assigned, copending application Ser. No. 809,803, herein incorporated by reference.

The following examples are intended only to further illustrate the invention and are not intended to limit the scope of the invention which is defined by the claims.

EXAMPLES 1-6

Nonwoody lignocellulosic materials within the scope of the invention were prepared for treatment by grinding in a Wiley mill to pass a 2-mm. screen. Each material was tested in four different media: (1) distilled water (pH 7.0); (2) distilled water adjusted to pH 11.5 with NaOH; (3) distilled water containing 1% (w/v) $H_2O_2$ adjusted to pH 7.0; and (4) distilled water containing 1% (w/v) $H_2O_2$ adjusted to pH 11.5 with NaOH. A 10-g. sample of the material to be treated was suspended in 500 ml. of reaction medium. The resultant slurry was stirred gently for 16-18 hr. at room temperature, adjusted to pH 7.0, and filtered to recover the solid fraction. A small portion of the wet, treated solids was weighed and then dried to constant weight to determine the moisture content. The swollen volume of the wet solids was measured by suspending a sample equivalent to 1 g. dry weight in a large excess of distilled water in a glass, graduated cylinder. The contents were thoroughly shaken and allowed to settle for 16-18 hr. The volume of the settled material to the nearest 0.5 ml. was recorded. The results are reported in the Table below.

It is understood that the foregoing detailed description is given merely by way of illustration and that modification and variations may be made therein without departing from the spirit and scope of the invention.

TABLE

| | | Swollen volume, ml./g. Treatment conditions | | | |
|---|---|---|---|---|---|
| Example | Substrate | pH 7.0 | pH 11.5 | 1% $H_2O_2$, pH 7.0 | 1% $H_2O_2$, pH 11.5 |
| 1 | wheat straw | 13.0 | 13.0 | 12.0 | 39.0 |
| 2 | wheat bran | 6.5 | 15.0 | 16.0 | 22.0 |
| 3 | corn bran | 7.0 | 11.0 | 7.0 | 25.0 |
| 4 | rice bran | 5.5 | 20.0 | 8.5 | 34.0 |
| 5 | sugar beet pulp[a] | 11.0 | 37.0 | 22.0 | 58.0 |
| 6 | orange pulp[b] | 6.0 | 95.0 | 39.0 | 137.0 |

[a]Dried residue of the sugar beet after extraction of the sucrose.
[b]Dried residue remaining after press extraction of juice from peeled oranges.

I claim:

1. A method for treating a substrate to yield a cellulosic product wherein said substrate is a nonwoody lignocellulosic portion of a fruit, root, or tuber, said method comprising treating said substrate in a reaction medium comprising an aqueous solution of strong alkali and hydrogen peroxide so as to solubilize at least a portion of the lignin and to enhance the water-binding capacity of the cellulose, thereby producing a water-soluble lignin-containing fraction and a water-insoluble cellulose-containing fraction, and recovering the water-insoluble fraction from the reaction medium as said cellulosic product.

2. A method as described in claim 1 wherein said substrate is sugar beet pulp.

3. A method as described in claim 1 wherein said substrate is citrus pulp.

4. A method as described in claim 1 wherein said substrate is seed hulls.

5. A method as described in claim 1 wherein said substrate is cereal bran.

6. A method as described in claim 1 wherein said strong alkali is sodium hydroxide, and the pH is controlled within the range of about 11.2 to about 11.8.

7. A method for treating a substrate to yield a cellulosic product wherein said substrate is a nonwoody lignocellulosic component of a plant, said method comprising treating said substrate in a reaction medium comprising an aqueous solution of strong alkali and hydrogen peroxide at a pH in the range of about 11.2 to about 11.8 so as to solubilize at least a portion of the lignin and to enhance the water-binding capacity of the cellulose, thereby producing a lignin-containing water-soluble fraction and a cellulose-containing water-insoluble fraction, and recovering the water-insoluble fraction from the reaction medium as said cellulosic product.

8. A method as described in claim 7 wherein said substrate is selected from the group consisting of sugar beet pulp, citrus pulp, seed hulls, and cereal bran.

9. A method as described in claim 8 wherein said strong alkali is sodium hydroxide.

10. The cellulosic product produced by the method of claim 1.

11. The cellulosic product produced by the method of claim 2.

12. The cellulosic product produced by the method of claim 3.

13. The cellulosic product produced by the method of claim 4.

14. The cellulosic product produced by the method of claim 5.

15. The cellulosic product produced by the method of claim 6.

16. The cellulosic product produced by the method of claim 7.

17. The cellulosic product produced by the method of claim 8.

18. The cellulosic product produced by the method of claim 9.

* * * * *